United States Patent [19]
Zachry, Jr.

[11] Patent Number: 5,181,280
[45] Date of Patent: Jan. 26, 1993

[54] STRAP RETAINER

[75] Inventor: Woodie M. Zachry, Jr., Spring, Tex.

[73] Assignee: Encon Safety Products, Houston, Tex.

[21] Appl. No.: 786,256

[22] Filed: Nov. 1, 1991

[51] Int. Cl.⁵ .............................................. A61F 9/02
[52] U.S. Cl. ........................................ 2/452; 24/170; 24/191
[58] Field of Search .................... 2/452, 426, 428, 440, 2/436, 437; 24/191, 170, 196

[56] References Cited

U.S. PATENT DOCUMENTS

| | | | |
|---|---|---|---|
| 3,605,204 | 9/1971 | Amundsen | 2/452 X |
| 4,567,628 | 2/1986 | Prete, Jr. et al. | 24/191 X |
| 4,607,398 | 8/1986 | Faulconer | 2/452 |
| 4,727,628 | 3/1988 | Rudholm | 24/191 X |
| 4,843,688 | 7/1989 | Ikeda | 24/170 |

OTHER PUBLICATIONS

Lab Safety Supply Catalog pp. 100, 101, 103.

Primary Examiner—Peter Nerbun
Attorney, Agent, or Firm—Kirk & Lindsay

[57] ABSTRACT

A strap retainer useful for attaching a retaining strap to safety equipment for quick positioning, securing and release of the equipment by the user is described. The strap retainer comprises a quick-release clamp on one end having a frame, a beveled stabilizer flange on the frame to position the retainer strap, a serrated edge, and a spring hinge cooperating to form an opening through which the retaining strap is drawn and held by the serrated edge being urged against the strap by the spring hinge. The strap retainer can be retrofitted to the safety equipment either by a clip or can be integrally constructed with an element of the equipment, usually safety googles.

8 Claims, 2 Drawing Sheets

STRAP RETAINER

FIELD OF THE INVENTION

The present invention relates to a quick release strap retainer, particularly useful for attaching a retaining strap to safety equipment worn by a person so that the equipment may be quickly positioned on the wearer in any situation, but especially during unexpected emergencies.

DESCRIPTION OF PRIOR ART

Retainers which attach a retaining strap to industrial safety and health equipment such as protective goggles, and the like are well known in industrial environments for safety purposes and in sports such as skiing and scuba diving. A quick release strap retainer is beneficial both for safety considerations as well as convenience of the wearer. Often, the safety equipment must be quickly positioned and the strap adjusted with enough tension so that the equipment fits securely on the wearer. Most commonly, the equipment will be face or eye protection; i.e. goggles. Protective goggles, which protect the eyes from outside material including hazardous liquids and chemical splashes, must have a retainer that securely holds the retaining strap so that the goggles remain in place over the eyes of the wearer forming a protective envelope in front of the eyes. It is important that the retainer also allow for quick release of the strap to reposition the goggles.

Previous attempts to develop satisfactory secure quick-release devices have met with failure or unsatisfactory performance largely because of slippage occurring thereby loosening the strap. A prior similar strap retainer used for dust and chemical respirators included a framed end unit clamp through which the retaining strap passed with a jaws-like fastener for holding the strap in place. The end unit fastener included a rectangle opening through which the goggle strap is drawn. A living hinge, urged a cover against the strap resting on a portion of the frame. While apparently satisfactory for respirators, unfortunately, the retaining strap is not held tightly in place by it and slippage occurs, particularly when goggles are worn. The strap loosens, thereby loosening the seal between the goggle and the face of the wearer so that the wearer must stop, often at a most inopportune or dangerous time, to readjust the goggle strap. It was both annoying, and unsafe. A secure device for holding the strap was needed.

SUMMARY OF THE INVENTION

The present invention accomplishes the objective of providing a new strap retainer that solves the problem of retainer strap slippage; the strap retainer of the present invention allows face gear or other equipment to be positioned quickly while providing a positive clamp on the strap which prevents strap loosening during wear. The strap retainer of this invention has a clamp with a beveled flange and carried by a frame and a hinge cooperating to form an opening through which the retaining strap is drawn, a means for attaching the strap retainer to the goggle, and a central segment connecting, and contiguous with, the clamp at one end and the means for attaching the retainer to the equipment at the other.

The surface of the flange facing the opening is beveled and helps overcome the problems of previous attempts to create a quick release, quick tightening secure retainer strap. The advantages of the beveled flange are twofold. First, it provides a surface against which the retaining strap, when in position is pressed over a greater surface area. Increased surface area contact provides increased friction between the retaining strap and the beveled side of the flange thereby decreasing slippage. Second, the spring type "living" hinge pushes a serrated edge of a cover on the opening down against the strap resting on the beveled surface.

The strap retainer of the present invention is especially useful with protective goggles. When not in use, the wearer often positions the protective goggle on top of his head, usually over a hardhat or other headgear. With the present invention, the wearer, especially during unanticipated emergencies, can quickly pull the goggle over the headgear, place it over the eyes and tighten the retaining strap by pulling the end of the strap back from the goggle face. In approximately 3 seconds, the person wearing the goggle has a secure facial seal that remains secure. Other equipment could similarly benefit from use of such a retainer.

DESCRIPTION OF THE PREFERRED EMBODIMENTS

The strap retainer of this invention is useful to persons who wear safety equipment such as goggles, face masks or respirators to protect the eyes and face from foreign, and often hazardous, materials. Such equipment is useful either in industry or sports such as scuba or skiing. The strap retainer of this invention simplifies the securing and adjusting of safety equipment making it more likely that workmen and sports participants will wear their equipment properly. This invention is especially useful in unanticipated emergencies where a protective goggle must be positioned over the eyes and securely sealed against the face in a matter of seconds. It is important that the retainer strap not loosen under tension so that the seal between the body of the goggles and the face of the wearer remain secure while the goggles are in place.

Figure 1:
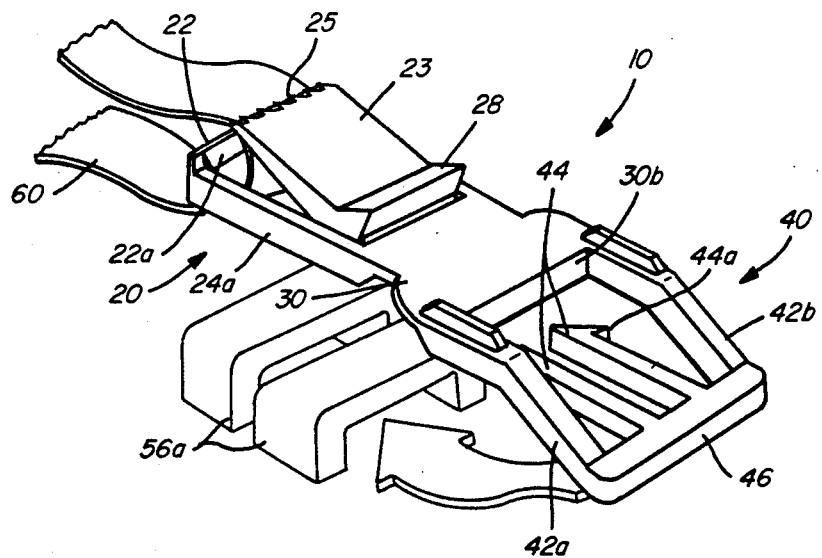
FIG. 1 is a perspective view of the strap retainer showing an arrow clip to secure the retainer to existing emergency facewear.
Figure 3:
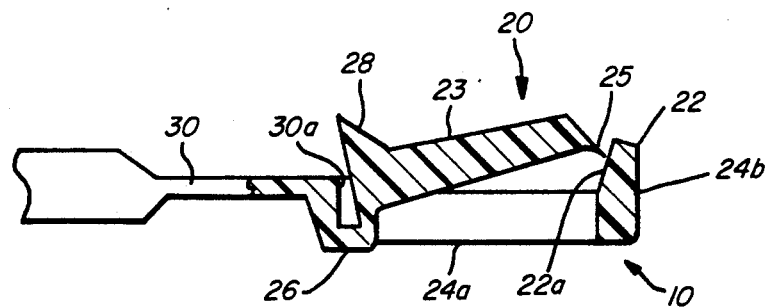
FIG. 3 is a side elevation of the clamp, partially in section, showing the flange and the living hinge in open position.
Figure 4:
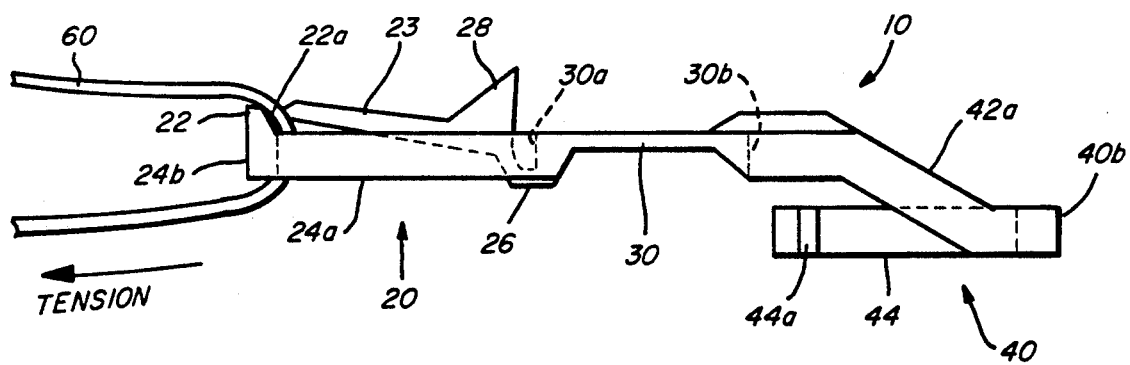
FIG. 4 is a side view of the strap retainer showing the strap being held by the serrated edge against the beveled surface of the flange.

The strap retainer 10 of this invention, is used for attaching a retaining strap 60 to equipment such as goggles 50 for quick positioning on the face of the wearer. Overall, the strap retainer 10 includes a clamp 20, an attaching means 40 for attaching the strap retainer 10 to the equipment, i.e. goggles 50 and a means for connecting 30 the clamp 20 and the attaching means 40. In the preferred embodiment, the means for connecting 30 is a central segment as shown in FIG. 1, for example. The clamp 20, the attaching means 40 and central segment 30 are easily molded in one piece from a tough flexible plastic material such as, for example, nylon, polyethylene, polypropylene, polyethylene/polyvinyl acetate copolymers, and the like. Some plastics are better than others, of course nylon is the plastic of preference. Selection of the proper material is within the skill of those in the art. The clamp 20 includes a frame 24, a flange 22, a moveable cover 23 with a tab 28 and a spring hinge 26 all of which cooperate to form an opening through which the retaining strap 60 (FIG. 4) is drawn and held once properly tensioned. The flange 22 (FIG. 3) is mounted on the frame 24 and is beveled so that the flange 22 has a sloped side facing the opening formed by the frame 24. The beveled surface is prepared to be about 5° to about 10°, most preferably, 7° from the plane of the flange. The serrated edge 25 of the movable cover 23 when closed upon strap 60 is urged against strap 60 by the action of hinge 26 on cover 23. The hinge 26 is well known as a "living hinge" and urges the serrated edge 25 against strap 60 thereby holding the restraining strap 60 against the beveled side 22a of the flange 22 (FIG. 4). The secured retention of strap 60 results from the cooperation of the clamp 20, the stabilizer flange 22, beveled surface 22a, and the tension of the goggle strap 60.

The clamp 20 preferably has a frame 24 with two longitudinal side members 24a extending from central segment 30 to flanged end 24b which form an opening, in FIG. 1 it is shown as being rectangular. The retaining strap 60 passes through the rectangular opening described by the frame 24. The moveable cover 23 substantially covers the opening formed by the frame 24 and attaches to the clamp 20 by the hinge 26. The house 20 is well known to those skilled in the art, and is integrally molded with the rest of the clamp 20. The movable cover 23 has a serrated edge 25 opposite the hinge 26 and facing the beveled surface 22a of the flange 22. After the retaining strap 60 (FIG. 4) is drawn through the opening of the clamp 20, the spring hinge 26 urges the cover 23 with its serrated edge 25 against the retaining strap 60 (FIG. 4) thereby tightly holding the retaining strap 60 between the serrated edge 25 and the beveled slope 22a of the flange 22.

The moveable cover 23 includes a releasing tab 28 to provide for quick release of the retaining strap 60 from the clamp 20. The tab 28 is adjacent to the spring hinge 26 so that when the wearer depresses the tab 28, the spring hinge 26 pivots about the edge 30a of the frame 24 and the serrated edge 25 rises away from the flange 22 and strap 60 thereby allowing the retaining strap 60 to be drawn through the opening.

To position the protective goggle 50, the wearer depresses the tab 28 of the flap 23 thereby raising the serrated edge 25 of the moveable cover 23 away from the beveled flange 22. The wearer then draws the retaining strap 60 through the opening in the frame 24 between the flange 22 and the serrated edge 25. After the wearer releases the tab 28, the ends of strap 60 are pulled to tension strap 60 while hinge 26 causes the serrated edge 25 to be urged against the strap 60 pressing it against the beveled surface 22a of the beveled flange 22. This bends the strap slightly further increasing the holding force created by the cooperation of the serrated edge 25 and the beveled surface 22a of flange 22. The wearer then pulls the end of the retaining strap 60 away from the face to tension the strap and easily adjust the goggle 50.

The strap retainer 10 of this invention may employ a number of attachment means 40. Three preferred attaching means 40 for attaching the retainer 10 to the equipment shown as a goggle body 56 in FIG. 2. The first embodiment allows the user to upgrade existing goggles by removing the strap from its existing keeper loops 56a (FIG. 1) and inserting an attaching means 40 shown as a pair of hooks 44 that engages with loops 56a on the sides of the goggle frame 56. The preferred hook 44 has one or more prongs 44a to engage 56 the loop 56a so that the strap retainer 10 is securely attached to the goggle frame 56. The prongs 44 extend towards the clamp 20 and are preferably offset from the plane of the frame 24 in the direction opposite the flange 22 as shown in FIG. 4. The shape and configuration of the attachment means 40 may vary widely. In the more preferred embodiment of this invention, attachment means 40 is shaped in the form of a rectangle with the one side 30b of the rectangle adjacent to the central segment 30 and a side opposite the central segment 30 having a transverse arm 46 and sides 42a and 42b with two protruding arrow shaped hooks 44. The end of each hook has a protruding flange 44a so to engage the loop 56a on the side of the goggle body 56 to secure the strap retainer 10 to the goggles 50. Preferably the longitudinal side arms 42a and 42b form an angle from the hooks 44 so that the plane of the hooks 44 is offset from the plane of the central segment 30 to accommodate hooking to loops 56a.

Figure 2:
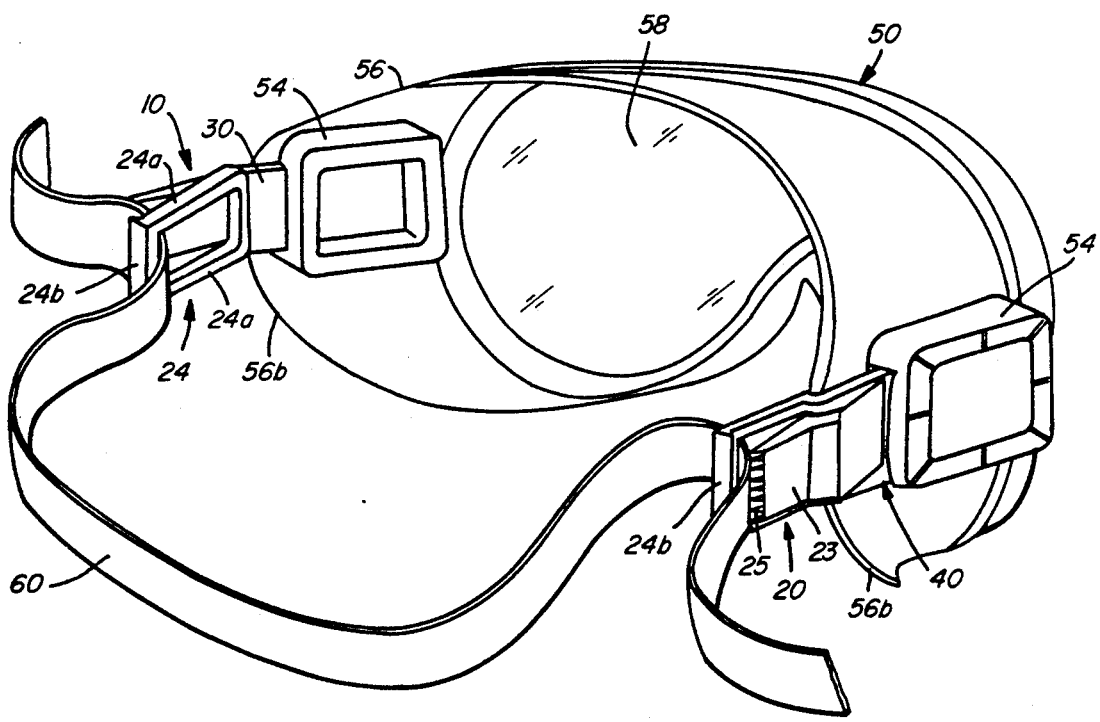
FIG. 2 is a perspective view of the strap retainer intergratably formed with a labyrinth vent assembly attached to a chemical splash goggle.

For newly manufactured equipment such as goggles shown in FIG. 2, attaching the strap retainer 10 to the goggles 50 may involve integrally molding the retainer 10 to the equipment in a single unit. In this embodiment, the protective goggle 50 has a goggle body 56 adapted to conform to the contours of the face of the wearer producing a cavity in front of the eyes behind goggle lens 58 mounted to the front of the goggle frame body 56. The attaching means 40 to attach the retainer 10 may be molded with the side 56b of the goggle body 56.

In the instance of chemical splash goggles shown in FIG. 2, a vent assembly 54 is mounted to the side 56b of goggle frame. Here again, the retainer 10 is integrally formed with the side 56b of the goggle frame 56. A preferred embodiment includes goggles with a labyrinthian vent assembly 54, as disclosed in Hewitt et al. U.S. Pat. No. 4,945,577, hereby incorporated by reference for all purposes. In this embodiment of the invention the strap retainer 10 is integrally formed with the vent assembly 54 (FIG. 2). The vent assembly 54 provides for ventilation of the goggles to prevent fogging of the lens or wearer discomfort while preventing the entry of splashed liquids into the protected area formed by the cavity.

The vent 54 integrally molded with the retainer 10 is attached to the body 56 of the goggles 50 in any acceptable manner, preferably as described in the mentioned U.S. Pat. No. 4,945,577.

The foregoing disclosure and description of the invention are illustrative and explanatory thereof, and various changes in the size, shape, combination and materials as well as the details of the illustrated construction may be made without departing from the scope of the invention. It is understood that the invention is not limited to the specific embodiments disclosed above for purposes of exemplification, but many modifications and changes will be apparent from the description and drawing without departing from the scope of the attached claims.

What is claimed is:

1. A quick adjustment and release retainer for attaching a strap to safety equipment for positioning the equipment with the strap under tension and quick release by the user comprising:

a clamp having a frame and a movable cover, the frame and moveable cover cooperating to hold the retaining strap securely in place on the wearer;

the frame forming an opening through which the retaining strap is drawn and having a flange, with a beveled surface facing the opening, positioned to engage the retaining strap when it is drawn through the opening and placed under tension;

the movable cover, sized to substantially cover the opening of the frame, attached to the clamp by a spring hinge, and having a serrated edge opposite the hinge, facing the beveled surface of the flange, the spring hinge adapted to urge the serrated edge against the retaining strap when the retaining strap is drawn through the opening and is in contact with the beveled surface of the flange to hold the equipment in position, the movable cover further having a means for releasing the retaining strap from the clamp;

a means to attach the retainer to equipment; and a means for connecting the clamp to the attaching means.

2. The retainer of claim 1 wherein the attaching means comprises a clip having a hook to engage an existing strap retainer on the equipment.

3. The retainer of claim 2 wherein the hook includes one or more prongs extending toward the clamp and offset from the plane of the frame in the direction opposite the beveled flange.

4. The retainer of claim 3 wherein the clip comprises two arrow shaped prongs carried by a transverse arm protruding toward the connecting means and two parallel longitudinal side arms joining the connecting means with the transverse arm.

5. Safety goggles comprising:

a body adapted to conform to the face of the wearer;

retainers for attaching to each end of the strap to hold the strap under tension and provide for quick release by the user, each retainer comprising:

a clamp having a frame and a movable cover, the frame and moveable cover cooperating to hold the retaining strap securely in place on the wearer;

the frame forming an opening through which the retaining strap is drawn and having a flange, with a beveled surface facing the opening, positioned to engage the retaining strap when it is drawn through the opening;

the moveable cover, sized to substantially cover the opening of the frame, attached to the clamp by a spring hinge, and having a serrated edge opposite the hinge, facing the beveled surface of the flange, the spring hinge adapted to urge the serrated edge against the retaining strap when the retaining strap is drawn through the opening and is in contact with the beveled surface of the flange; the movable cover further having a tab adjacent to the hinge so that depression of the tab releases the retaining strap from the clamp;

a central segment connected to the frame of the clamp forming one end of the opening, the frame having two longitudinal side members contiguous with and extending from the central segment and an end opposite the central segment joining the two side members and carrying the beveled flange; and a means for attaching the retainers to the goggles.

6. The goggles of claim 5 wherein the means for attaching the retainer comprises a transverse arm with two protruding arrow shaped prongs pointed toward the central segment and joined to two longitudinal side arms which extend from the central segment and bend at an obtuse angle away from the arrow prongs so that the plane of the arrow prongs is offset from the plane of the central segment to accommodate hooking to one or more loops on the equipment.

7. The goggles of claim 5 wherein the attaching means is integrally formed with the clamp.

8. The goggles of claim 5 wherein the means for attaching the retainers to the goggle is a labyrinth vent assembly, with which the clamp is molded, mounted to a side of the goggle body.

* * * * *